US012791767B2

(12) United States Patent
Batchelor et al.

(10) Patent No.: US 12,791,767 B2
(45) Date of Patent: Nov. 10, 2026

(54) LOW ADHESION SURFACES AND METHOD FOR SCOPES

(71) Applicant: GYRUS ACMI, INC., Westborough, MA (US)

(72) Inventors: Kester Julian Batchelor, Mound, MN (US); Teo Heng Jimmy Yang, Heath (GB)

(73) Assignee: Gyrus ACMI, Inc., Westborough, MA (US)

( * ) Notice: Subject to any disclaimer, the term of this patent is extended or adjusted under 35 U.S.C. 154(b) by 902 days.

(21) Appl. No.: 17/650,944

(22) Filed: Feb. 14, 2022

(65) Prior Publication Data

US 2022/0260757 A1 Aug. 18, 2022

Related U.S. Application Data

(60) Provisional application No. 63/270,360, filed on Oct. 21, 2021, provisional application No. 63/149,935, filed on Feb. 16, 2021.

(51) Int. Cl.

*G02B 1/18* (2015.01)
*A61B 1/00* (2006.01)
*G02B 1/12* (2006.01)
*G02B 1/14* (2015.01)

(52) U.S. Cl.

CPC .............. *G02B 1/18* (2015.01); *A61B 1/0008* (2013.01); *A61B 1/00096* (2013.01); *A61B 1/0011* (2013.01); *G02B 1/12* (2013.01); *G02B 1/14* (2015.01)

(58) Field of Classification Search

CPC ............ A61B 1/00096; A61B 1/00098; C09D 5/1681; C09D 183/04; C09D 183/06; C09D 183/08; G02B 1/118; G02B 1/12; G02B 1/18; G02B 1/115; G02B 1/116

See application file for complete search history.

(56) References Cited

U.S. PATENT DOCUMENTS

2003/0023190 A1* 1/2003 Cox .................. A61M 25/0045 600/585
2004/0208791 A1* 10/2004 Extrand ................. B82Y 30/00 428/156
2008/0107868 A1* 5/2008 Kuroda ..................... B32B 3/10 428/141

(Continued)

FOREIGN PATENT DOCUMENTS

JP 2014087541 A * 5/2014

OTHER PUBLICATIONS

Product information AEROSIL RX 200, Apr. 2021, Evonik Operations GmbH, pp. 1-2. (Year: 2021).*

(Continued)

*Primary Examiner* — Michael J Carey
*Assistant Examiner* — Stephen Floyd London
(74) *Attorney, Agent, or Firm* — Schwegman Lundberg & Woessner. P.A.

(57) ABSTRACT

A medical device and associated methods are disclosed. In one example, the medical device includes an endoscope lens. In one example, the medical device includes a regular periodic physical structure. Examples of regular periodic physical structure may be formed from a bulk material of a component such as a lens, or a regular periodic physical structure may be formed as a coating.

13 Claims, 11 Drawing Sheets

(56) References Cited

U.S. PATENT DOCUMENTS

| | | | | |
|---|---|---|---|---|
| 2008/0228035 | A1* | 9/2008 | Hagihara | A61B 1/127 600/176 |
| 2012/0029514 | A1* | 2/2012 | Fairbourn | A61L 31/022 606/41 |
| 2015/0196940 | A1* | 7/2015 | Aizenberg | C09D 5/1681 428/141 |
| 2015/0289751 | A1* | 10/2015 | Frerck | A61B 1/127 264/293 |
| 2017/0340195 | A1* | 11/2017 | Daidoji | A61B 1/012 |
| 2019/0150955 | A1* | 5/2019 | Li | A61B 17/1622 |
| 2020/0174371 | A1* | 6/2020 | Duan | B05D 1/02 |
| 2020/0326457 | A1* | 10/2020 | Jeon | G02B 1/18 |
| 2020/0341169 | A1* | 10/2020 | Nakamatsu | C08K 3/36 |
| 2021/0015345 | A1* | 1/2021 | Yamada | G02B 1/18 |
| 2022/0175224 | A1* | 6/2022 | Sorensen | A61B 1/05 |
| 2022/0330802 | A1* | 10/2022 | Watanbe | A61B 1/00094 |
| 2022/0409034 | A1* | 12/2022 | Takasaki | A61B 1/126 |
| 2023/0123436 | A1* | 4/2023 | Komukai | A61B 1/126 600/157 |

OTHER PUBLICATIONS

Kreeft, Davey, "Review of Techniques to Achieve Optical Surface Cleanliness and Their Potential Application to Surgical Endoscopes".

* cited by examiner

LOW ADHESION SURFACES AND METHOD FOR SCOPES

CLAIM OF PRIORITY

This patent application claims the benefit of priority, under 35 U.S.C. § 119(e), to U.S. Provisional Patent Application Ser. No. 63/149,935, entitled "ULTRAHYDROPHOBIC SURFACES AND METHOD FOR SCOPE LENSES," filed on Feb. 16, 2021, and U.S. Provisional Patent Application Ser. No. 63/270,360, entitled "LOW ADHESION SURFACES AND METHOD FOR SCOPES," filed on Oct. 21, 2021, both of which are hereby incorporated by reference herein in their entirety.

TECHNICAL FIELD

Embodiments described herein generally relate to medical devices. Specific examples of medical devices include endoscopes.

SUMMARY

The inventors have discovered that several medical devices will benefit from a reduction in adhesion of material to one or more surfaces. For example, in endoscopes, components such as lenses may become fouled, fogged, or otherwise occluded by body fluids and/or tissue. Improved endoscopes and other medical devices with reduced adhesion surfaces are desired.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DESCRIPTION OF EMBODIMENTS

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Figure 1:
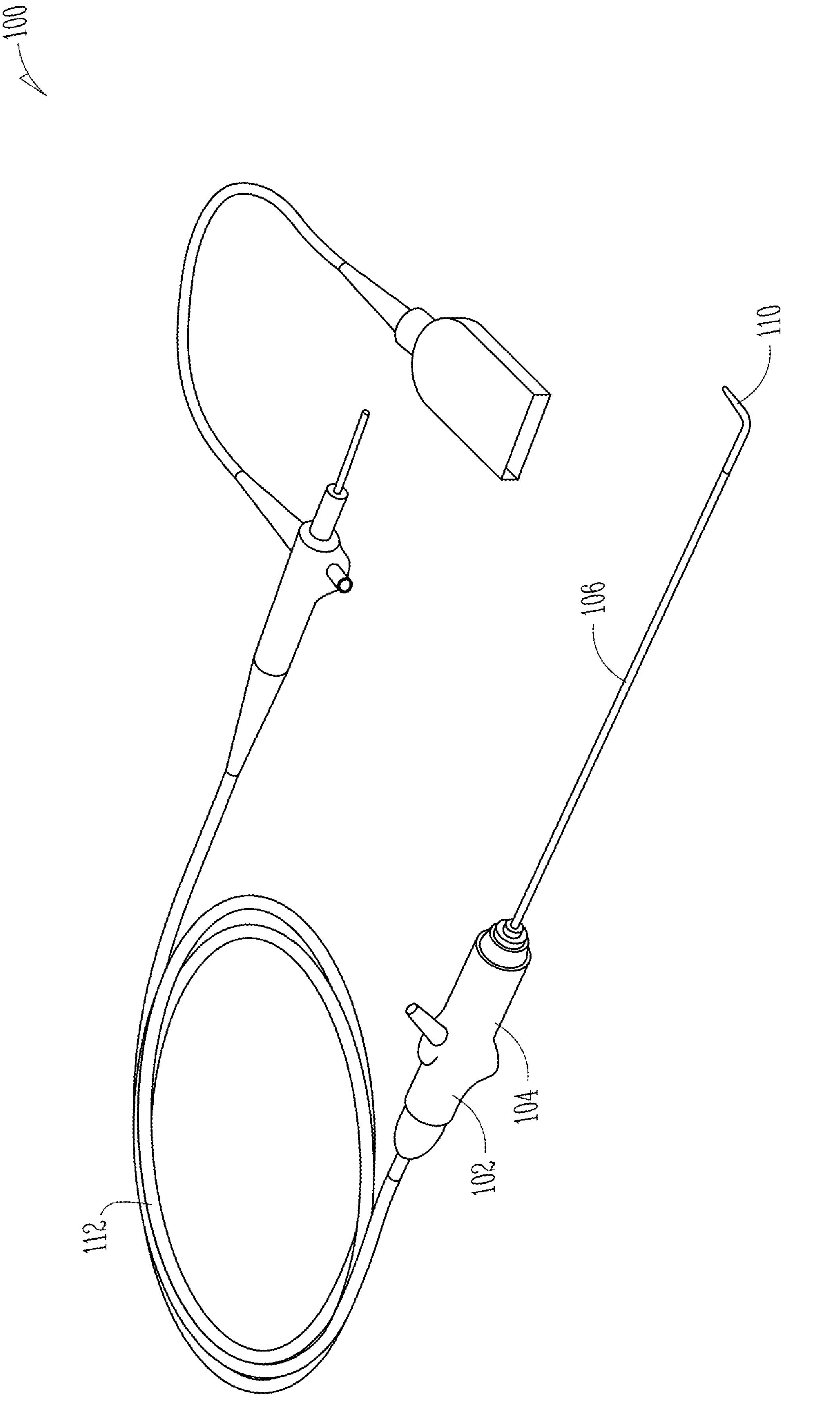
FIG. 1 shows an endoscopy system in accordance with some example embodiments.

FIG. 1 illustrates an example medical device that includes a surface with a regular periodic physical structure. Depending on the specific materials chosen, and the geometry of the regular periodic physical structure, the surface can be formed as hydrophobic, or hydrophilic. Although the terms hydrophobic and hydrophilic refer to interactions with water, the invention is not so limited. Regular periodic physical structure, as described in the present disclosure, also applies to other liquids and body fluids of note in medical procedures, such as oils or fats. A quantified degree of hydrophobicity and hydrophilicity will depend on the selected liquid and the selected coating or substrate forming the regular periodic physical structure.

The device of FIG. 1 shows an endoscope 100. The endoscope 100 includes a handle 102, a body 104, and a lumen 106 having a distal portion 110. The body 104 may include circuitry and/or imaging devices to operate the endoscope 100. In selected examples, some or all operating circuitry may be included in a cart (not shown) that is coupled to the endoscope through connection cable 112. The lumen 106 may include more than one lumen inside one another, and may include additional devices that pass through one or more lumens.

Figure 2:
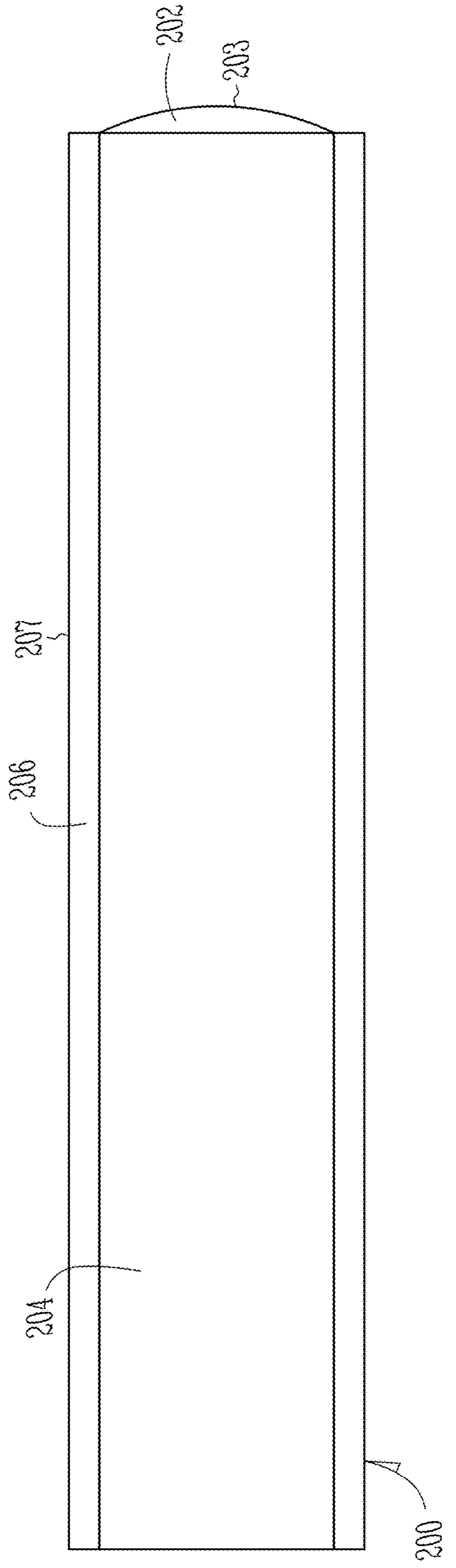
FIG. 2 shows a distal portion of an endoscope in accordance with some example embodiments.

FIG. 2 shows a portion of a lumen 200 similar to lumen 106 from FIG. 1. The example lumen 200 includes a core 204 for optical transmission, and a lens region 202 at a distal portion of the core 204. In one example, the core 204 includes a transparent or otherwise optically transmissible material. Examples of transparent material include, but are not limited to, glasses and polymers. Examples of glass materials include silicon dioxide glasses, and other glasses.

In one example, the lens region 202 is part of a bulk material that is an integral part of the core 204. In one example, the lens region 202 is a separate component that is attached to the distal portion of the core 204. In one example, the lens region 202 is formed from the same material as the core 204 although it may be a separate component. In one example, the lens region 202 is formed from a different material from the core 204. A different material may provide desirable optical properties such as a different refractive index that may provide magnification advantages. In examples where the lens region 202 is a separate component, an adhesive may be present at an interface between the lens region 202 and the core 204.

In one example, a surface 203 on the lens region 202 includes a regular periodic physical structure. In the present disclosure, the term regular periodic physical structure may include one or more protrusions or asperities. The concepts described are applicable to hydrophobic and superhydrophobic physical structures and coatings, and therefore these terms may be used interchangeably herein unless otherwise noted. The concepts described are also applicable to hydrophilic and superhydrophilic physical structures and coatings, and therefore these terms may be used interchangeably herein unless otherwise noted. The term regular periodic physical structure may include a pattern of protrusions or asperities as described in more detail below. In one example, the term regular periodic physical structure is in contrast to a chemical coating, lubricant, or other hydrophobic or hydrophilic layer whose principal of operation is based on chemistry. In one example, regular periodic physical structure includes nanoscale structures that provide hydrophobicity or hydrophilicity as described in more detail below.

Although a single lens is shown as part of the lens region 202, the invention is not so limited. Multiple lenses may be used in combination with one another at the lens region. In such an example, one or more of the multiple lenses may include a regular periodic physical structure as described. In multiple lens examples, lenses may be located within the distal portion, but not all lenses are necessarily located at a very distal end.

In one example, as illustrated in FIG. 2, a shield 206 is included around all or part of the core 204. One example of a shield includes a separate structure, such as a tube that the core is inserted into. Another example of a shield 206 includes one or more coatings around all or part of the core 204. Suitable materials for the shield 206 include polymer materials, glass materials, ceramic materials, etc. In one example, the shield is opaque and may help to contain optical transmission within the core 204. In one example, the shield provides mechanical resilience and protects the core 204 from damage.

In one example, a surface 207 on the shield 206 includes a regular periodic physical structure. In one example, regular periodic physical structure includes nanoscale structures that provide hydrophobicity or hydrophilicity as described in more detail below. In one example, the regular periodic physical structure on the surface 207 of the shield 206 is different than the regular periodic physical structure on the surface 203 of the lens region 202. In one example, the regular periodic physical structure on the surface 207 of the shield 206 is the same as the regular periodic physical structure on the surface 203 of the lens region 202.

It may be beneficial to have different regular periodic physical structure on different surfaces of components of the endoscope. For example, a high quality regular periodic physical structure may be used on the surface 203 of the lens region 202 that provides minimal optical distortion and/or high optical transmission. A less expensive regular periodic physical structure may be used on less critical surfaces, such as the surface 207 on the shield 206.

Figure 3:
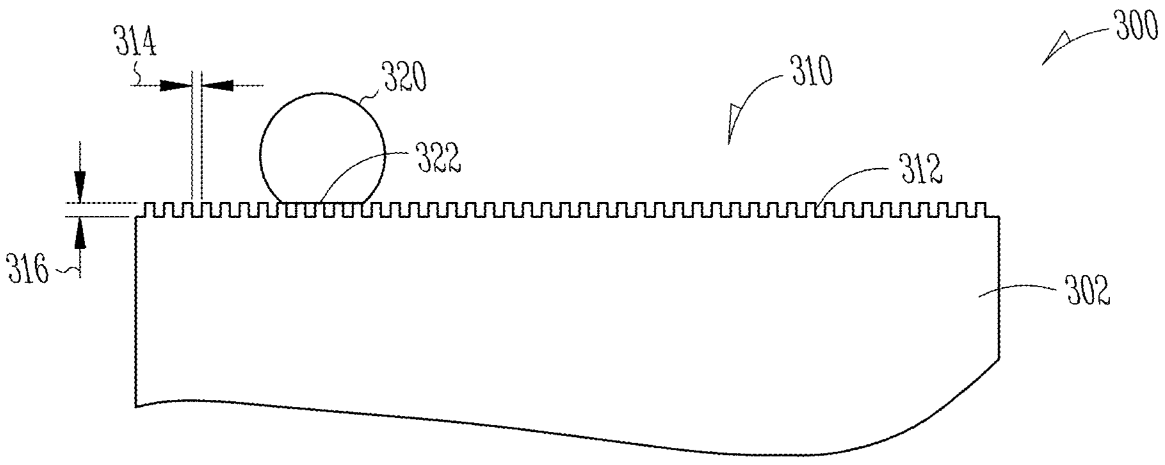
FIG. 3 shows a surface including a regular periodic physical structure in accordance with some example embodiments.

FIG. 3 shows one example of a surface with a regular periodic physical structure 310 on a substrate 302. As discussed in examples above, the regular periodic physical structure 310 may be on all or a portion of a surface, and different regular periodic physical structure 310 may be used on different surfaces or components of an endoscope. For example, the regular periodic physical structure 310 may be on an entire outer surface of a lumen of an endoscope. The regular periodic physical structure 310 may be on only a portion of an outer surface of a lumen. The regular periodic physical structure 310 may be on all or a portion of a lens of an endoscope.

As shown in FIG. 3, in one example, the regular periodic physical structure 310 includes asperities 312 having a height 316 and a pitch 314. The regular periodic physical structure 310 can be described by the following equation:

$$\Lambda_C = \frac{-\rho g V^{1/3}\left(\left(\frac{1-\cos(\theta_a)}{\sin(\theta_a)}\right)\left(3+\left(\frac{1-\cos(\theta_a)}{\sin(\theta_a)}\right)^2\right)\right)^{2/3}}{(36\pi)^{1/3}\gamma\cos(\theta_{a,0}+w-90)}$$

where $\Lambda$ is a contact line density, and $\Lambda_c$ is a critical contact line density; $\rho$=density of the liquid droplet; g=acceleration due to gravity; V=volume of the liquid droplet; $\theta_a$=advancing apparent contact angle; $\theta_{a,0}$=advancing contact angle of a smooth substrate; $\gamma$=surface tension of the liquid; and w=tower wall angle.

The contact line density $\Lambda$ is defined as a total perimeter of asperities over a given unit area.

In one example, if $\Lambda > \Lambda_c$ then a droplet 320 of liquid are suspended in a Cassie-Baxter state. Otherwise, the droplet 320 will collapse into a Wenzel state. In one example when a Cassie-Baxter state is formed, an ultra-hydrophobic condition exists, and a low adhesion surface is formed. FIG. 3 illustrates a Cassie-Baxter state, where the droplet 320 rests on top of the asperities 312 at interface 322. Although rectangular asperities are shown for illustration purposes, the invention is not so limited. Asperity shapes are taken into account in the formula above, at least in the tower wall angle (w) term.

In the example of FIG. 3, the asperities are formed directly from a bulk material, and are not formed from a separate coating. One method of forming asperities directly from a bulk material includes chemical etching. Another example of forming asperities directly from a bulk material includes laser etching or ablation. Another example of forming asperities directly from a bulk material includes ion etching.

Figure 4:
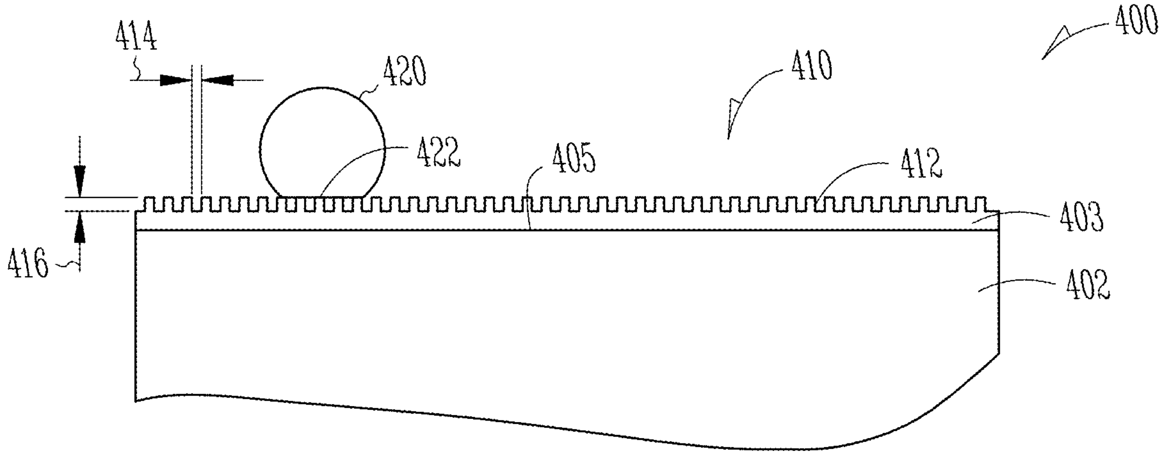
FIG. 4 shows another surface including a regular periodic physical structure in accordance with some example embodiments.

FIG. 4 shows another example of a surface regular periodic physical structure 410 on a substrate 402. As discussed in examples above, the regular periodic physical structure 410 may be on all or a portion of a surface, and different regular periodic physical structure 410 may be used on different surfaces or components of an endoscope. For example, the regular periodic physical structure 410 may be on an entire outer surface of a lumen of an endoscope. The regular periodic physical structure 410 may be on only a portion of an outer surface of a lumen. The regular periodic physical structure 410 may be on all or a portion of a lens of an endoscope.

As shown in FIG. 4, in one example, the regular periodic physical structure 410 includes asperities 412 having a height 416 and a pitch 414. However, in the example of FIG. 4, the regular periodic physical structure 410 is formed as part of a coating 403 that forms a direct interface 405 with substrate 402. FIG. 4 illustrates a Cassie-Baxter state, where the droplet 420 rests on top of the asperities 412 at interface 422.

In one example, the asperities 412 are formed by application of nanoparticles to a surface of the substrate 402 to form the coating 403. In one example, the asperities 412 are formed by application of nanoparticles to a surface of the coating 403. In one example, the nanoparticles include hexamethyldisiloxane (HMDSO) particles. In one example, the nanoparticles include tetramethyldisiloxane (TMDSO) particles. In one example, the nanoparticles include fluorosilane particles. Other nanoparticle materials are also within the scope of the invention.

In one example, a hydrophobic chemistry of the nanoparticle, in combination with a nano scale asperity structure as shown in FIG. 4 provide better hydrophobicity compared to a hydrophobic chemistry alone. In one example, a hydrophilic chemistry of a nanoparticle, in combination with a hydrophilic nano scale asperity structure provide better hydrophilicity compared to a hydrophilic chemistry alone.

Figure 5:
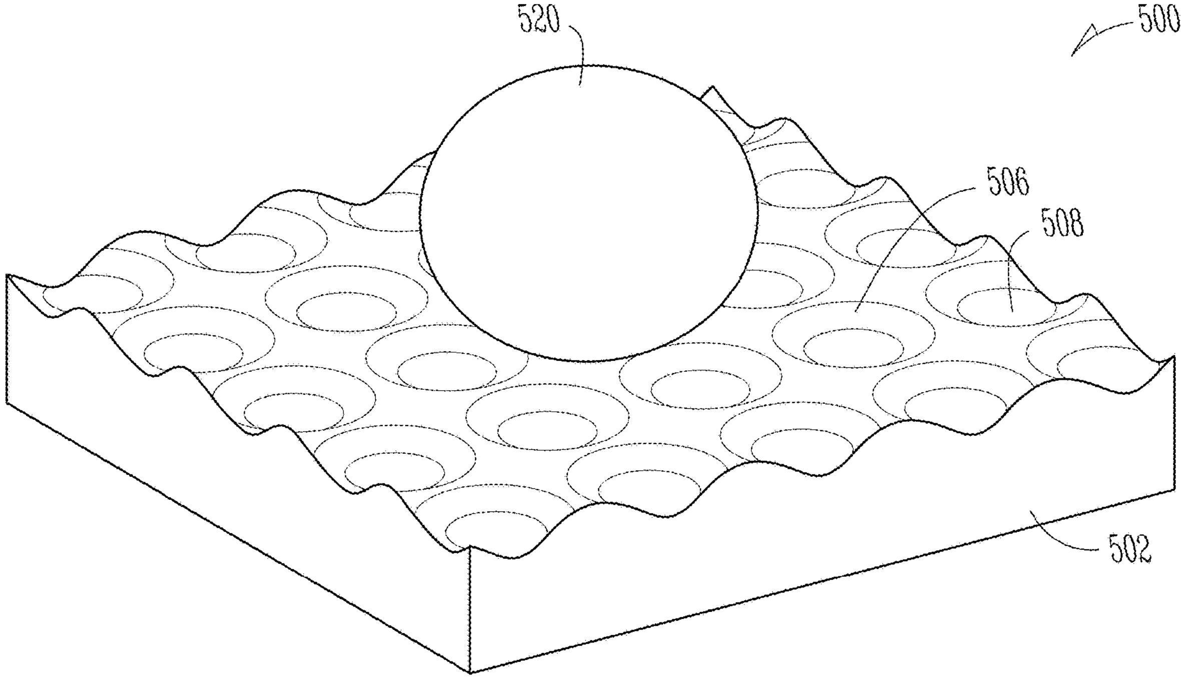
FIG. 5 shows another surface including a regular periodic physical structure in accordance with some example embodiments.

FIG. 5 shows one example of a laser etched surface 500 that includes regular periodic physical structure as described above. In the example of FIG. 5, a gaussian hole array is formed by applying laser energy to a surface of a substrate 502 in a controlled regular pattern to form holes 506. A shape of the holes 506 is characterized as gaussian due to the energy distribution of laser energy in forming the array. In the example shown, a number of asperities 508 are formed in the process that may be spaced and arranged in an array that provides a Cassie-Baxter state as described above. A liquid droplet 520 is illustrated on the regular periodic physical structure similar to the droplet 320 from FIG. 3, or the droplet 420 from FIG. 4.

FIGS. 6A-6D show four different examples of regular periodic physical structure formed on a surface, such as a coating surface, or a surface of a bulk material. Physical dimensions of the regular periodic physical structure dictate different states of interaction with a liquid, such as water, or other fluids. One of ordinary skill in the art, having the benefit of the present disclosure, will recognize that the variable of surface tension $\gamma$ as used in the equation above, is at least partially determined by material properties such as surface energy, and that a surface condition as shown in FIGS. 6A-6D depends in part on a choice of material in both a substrate and a liquid medium.

Figure 6A:
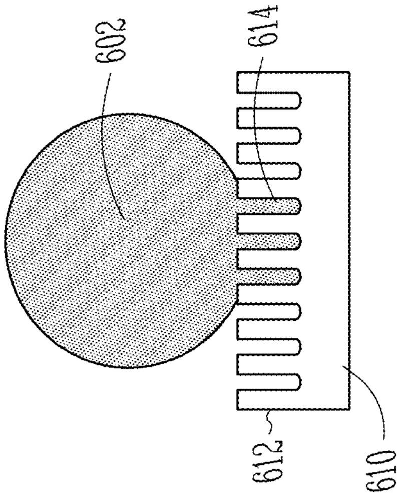
FIG. 6A shows another surface including a regular periodic physical structure in accordance with some example embodiments.

FIG. 6A shows a Wenzel state of interaction. A substrate 610 and a liquid medium 602 in a droplet form are shown. The substrate 610 includes a plurality of asperities 612 that are regularly spaced and define a number of spaces 614 between asperities 612. The substrate 610, asperities 612, and spaces 614 can be characterized by the equation above.

Figure 6B:
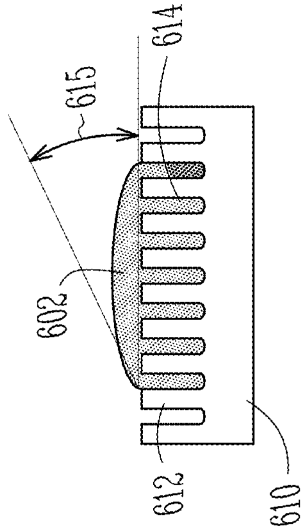
FIG. 6B shows another surface including a regular periodic physical structure in accordance with some example embodiments.

In FIG. 6A, the asperities 612 define a contact line density $\Lambda$ that is less than the critical contact line density $\Lambda_c$. As such, in FIG. 6A, a portion of the liquid medium 602 penetrates into the spaces 614 between asperities 612 in the regular periodic physical structure. FIG. 6B shows a hydrophilic Wenzel state where a contact angle 615 is less than 90 degrees. In one example, the superhydrophilic state is defined by a contact angle 615 less than 10 degrees. In lower contact angle states, the water or other fluid on and within the regular periodic physical structure facilitates fast dispersal of any additional fluid or contaminant that may come into contact with the surface. In a surgical context, material such as blood, tissue, etc. will be more easily flushed from a surface due the water within the hydrophilic regular periodic physical structure providing a lubrication or material transport effect. In a more preferred example, the superhydrophilic state is defined by a contact angle 615 less than 5 degrees. The lower contact angle provides lower resistance to lateral movement across the surface of material such as blood or tissue that is desired to be cleared from a local region.

Figure 6C:
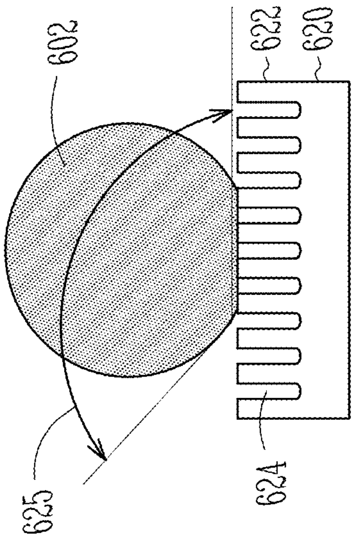
FIG. 6C shows another surface including a regular periodic physical structure in accordance with some example embodiments.

FIG. 6C shows a Cassie-Baxter state of interaction, similar to the state shown in FIGS. 3-5 above. A substrate 620 and a liquid medium 602 in a droplet form are shown. The substrate 620 includes a plurality of asperities 622 that are regularly spaced and define a number of spaces 624 between asperities 622. The substrate 610, asperities 622, and spaces 624 can be characterized by the equation above.

In FIG. 6C, the asperities 622 define a contact line density $\Lambda$ that is greater than the critical contact line density $\Lambda_c$. As such, in FIG. 6C, none or very little of the liquid medium 602 penetrates into the spaces 624 between asperities 622 in the regular periodic physical structure. FIG. 6C shows a hydrophobic Cassie-Baxter state where a contact angle 625 is greater than 90 degrees. In one example, a hydrophobic state is defined by a contact angle 625 between 90 and 150 degrees. In one example, a more preferred hydrophobic state is defined by a contact angle 625 between 100 and 140 degrees.

In one example, a range of 100 to 140 provides a desired degree of low adhesion, as indicated by a higher contact angle, while also providing a robust coating that is not easily worn off a surface. Some materials with a lower contact angle are more robust than materials with a higher contact angle, therefore a tradeoff in material wear versus low adhesion is balanced with a range between 100 and 140 degrees.

In one example, the superhydrophobic state is defined by a contact angle 625 greater than 150 degrees. In higher contact angle states, a fluid in contact with the regular periodic physical structure rides up on top of the asperities 622 with a low surface area of actual interfacial contact, which facilitates fast dispersal of any fluid or contaminant that may come into contact with the surface. In a surgical context, material such as blood, tissue, etc. will be more easily flushed from a surface due riding on top of the regular periodic physical structure. In a more preferred example, the superhydrophobic state is defined by a contact angle 625 greater than 160 degrees. The higher contact angle provides lower resistance to lateral movement across the surface of material such as blood or tissue that is desired to be cleared from a local region.

Figure 6D:
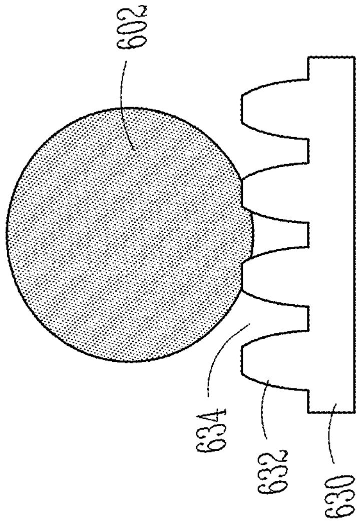
FIG. 6D shows another surface including a regular periodic physical structure in accordance with some example embodiments.

FIG. 6D shows a Lotus state of interaction. A substrate 630 and a liquid medium 602 in a droplet form are shown. The substrate 630 includes a plurality of asperities 632 that are regularly spaced and define a number of spaces 634 between asperities 632. The substrate 634, asperities 632, and spaces 634 can be characterized by the equation above. In the Lotus state, the liquid medium 602 is prevented from entering the spaces 634 between the asperities 632, resulting in low contact angle hysteresis (CAH) of less than 5 degrees at the moment a droplet runs off a substrate as defined below.

Figure 7A:
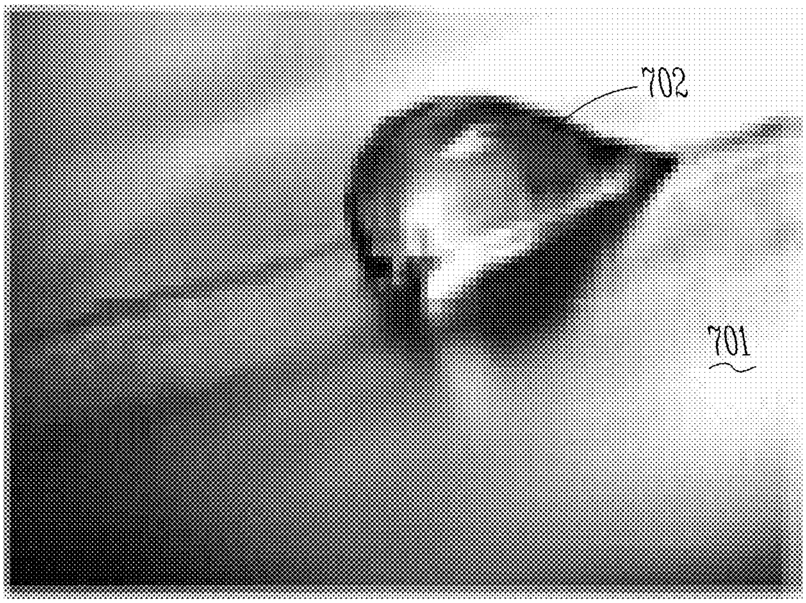
FIG. 7A shows a test surface including a regular periodic physical structure in accordance with some example embodiments.
Figure 7B:
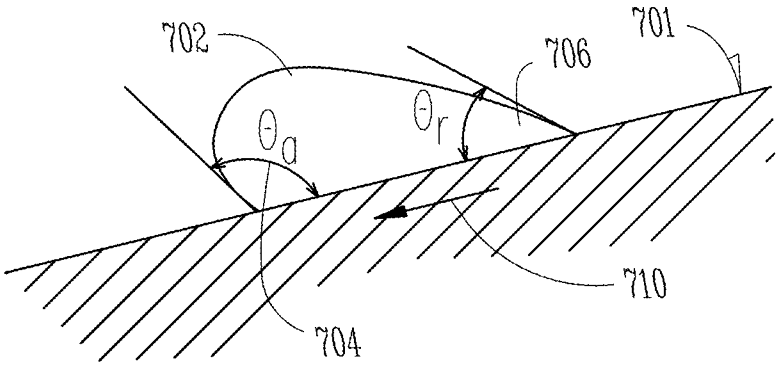
FIG. 7B shows an illustration of a testing protocol for quantifying a regular periodic physical structure in accordance with some example embodiments.

FIGS. 7A and 7B show a second method of quantifying a surface with regular periodic physical structure in addition to the equation above. In FIG. 7A, a droplet 702 is shown on a substrate 701. Examples of substrates 701 include coatings or processed bulk surfaces such that a surface of the substrate 701 forming an interface with the droplet 702 includes regular periodic physical structure as described in examples above. In a testing procedure, the substrate is tilted to an angle, and at some amount of tilting, the droplet ceases to adhere in its location, and runs off the substrate 701.

FIG. 7B shows an advancing contact angle 704 and a receding contact angle 706 of the droplet 702 as the substrate 701 is tilted. When the droplet runs off the substrate, it moves in direction 710. In a testing procedure, a difference can be measured between the advancing contact angle 704 and the receding contact angle 706. This difference is defined as the contact angle hysteresis (CAH).

In one example, if the CAH at the moment the droplet 702 runs off the substrate 701 is less than 5 degrees, then the material is nonadhesive. In one example, if the CAH at the moment the droplet 702 runs off the substrate 701 is greater than 5 degrees, then the material is adhesive.

The description above with respect to FIGS. 3-5, 6A-6D, and 7A-7B are used to quantify and specifically describe surfaces with regular periodic physical structure that exhibit low adhesion in medical devices. The surfaces may include hydrophilic behavior or hydrophobic behavior depending on the geometry and spacing of asperities as described above. As previously noted, specific surfaces may include, but are not limited to, lenses, parts of lumens, or entire surfaces of lumens.

In one example a fluorophore is added to a coating or a regular periodic physical structure that exhibits low adhesion in medical devices. Due to transparency and a very thin nature of regular periodic physical structure, it can be difficult during manufacturing to detect a presence or absence of the regular periodic physical structure. The addition of one or more fluorophores facilitates easy detection, by providing a luminescence in the presence of electromagnetic radiation at a wavelength known to elicit a fluorescent emission from the fluorophore. If a fluorescent emission is observed, the presence of a coating or a regular periodic physical structure is visually confirmed.

The one more fluorophores are present in a coating or a regular periodic physical structure in any amount suitable to provide a visual fluorescent emission. For example, the one or more fluorophores can be present at less than about 10 wt % of a coating or a regular periodic physical structure, less than about 5 wt % of a coating or a regular periodic physical structure, or in a range of from about 0.1 wt % to about 10 wt % of a coating or a regular periodic physical structure or in a range of from about 2 wt % to about 4 wt % of a coating or a regular periodic physical structure. The one or more fluorophores can be homogenously distributed about a coating or a regular periodic physical structure.

Alternatively, the one or more fluorophores are heterogeneously distributed about a coating or a regular periodic physical structure. A homogenous distribution of the fluorophores can be helpful to confirm that a coating or a regular periodic physical structure is present across the entirety of a coating or a regular periodic physical structure. A heterogenous distribution of the one or more fluorophores, however, can be helpful if the fluorophores are located within a portion of a coating or a regular periodic physical structure that is of particular interest and a user only wants to confirm that that a coating or a regular periodic physical structure is present at that location. Additionally, a heterogenous distribution of a coating or a regular periodic physical structure, can save on costs since a smaller amount of fluorophore can be included compared to an amount of the one or more fluorophores required to provide a homogenous distribution of the one or more fluorophores.

The one or more fluorophores of a coating or a regular periodic physical structure can include the same fluorophore disposed therein. Alternatively, a coating or a regular periodic physical structure can include different fluorophores. The degree of similarity between fluorophores can relate to their chemical composition, the wavelength or range of wavelengths of electromagnetic radiation the fluorophore absorbs, the wavelength or range of wavelengths of electromagnetic radiation the fluorophore emits, or both.

Including different fluorophores can be beneficial for various non-limiting reasons. For example, if a medical device includes different coatings or a regular periodic physical structure (e.g., different compositions) each coating or regular periodic physical structure can have a respective different fluorophore. The different fluorophores, for example, can emit electromagnetic radiation having different wavelengths. Therefore, the presence of the different coatings or regular periodic physical structures can be confirmed.

In some other examples, if a coating or a regular periodic physical structure is disposed on a substrate in a plurality of stacked layers, each layer can have a different fluorophore distributed therein. Therefore, the presence of each layer can be confirmed by observing the electromagnetic radiation associated with each fluorophore in their respective layer.

The fluorophores can also help to determine the thickness of a coating or a regular periodic physical structure. For example, if a coating or a regular periodic physical structure includes a homogeneous distribution of fluorophores, the electromagnetic emissions from the fluorophores can be quantified and associated with their respective depth within the thickness. Alternatively, X-ray fluorescence can be used to determine the respective depth of the fluorophores within the thickness.

There are a wide array of fluorophores that can be used in association with a coating or a regular periodic physical structure. Although the one or more fluorophores are generally disposed within a coating or a regular periodic physical structure (e.g., the exterior surface of anti-stick coating is free of the one or more fluorophores), it can be desirable for the fluorophores to be biocompatible. Biocompatibility is generally understood to relate to a material possessing the quality of being free of toxic or injurious effects on biological systems. If the fluorophores are biocompatible, they can be disposed on the exterior of a coating or a regular periodic physical structure. Additionally, if the fluorophores are biocompatible, it can mitigate harm caused by exposing the fluorophores to the body if a coating or a regular periodic physical structure is damaged or an interior of a coating or a regular periodic physical structure is exposed.

The fluorophores that can be included in a coating or a regular periodic physical structure can include an organic non-protein fluorophore, an organic dye, a nucleic acid dye, a fluorescent protein, or a mixture thereof. Examples of organic non-protein fluorophores include, but are not limited to, xanthene, cyanine, squaranine, squarine rotaxane, naphthalene, coumarin, oxadiazole, anthracene, pyrene, oxazine, acridine, arylmethine, tetrapyrrole, dipyrromethene, a derivative of any one of the preceding, or a mixture thereof. Examples of organic dyes include hydroxycoumarin, aminocoumarine, methoxycoumarine, allophycocyanin, or a mixture thereof. Examples of nucleic acid dyes include 4',6-diamidino-2-phenylindole, plicamycin, toyomycin, ethidium bromide, propidium iodide, or a combination thereof. An example of a fluorescent protein includes a green fluorescent protein.

Figure 11:
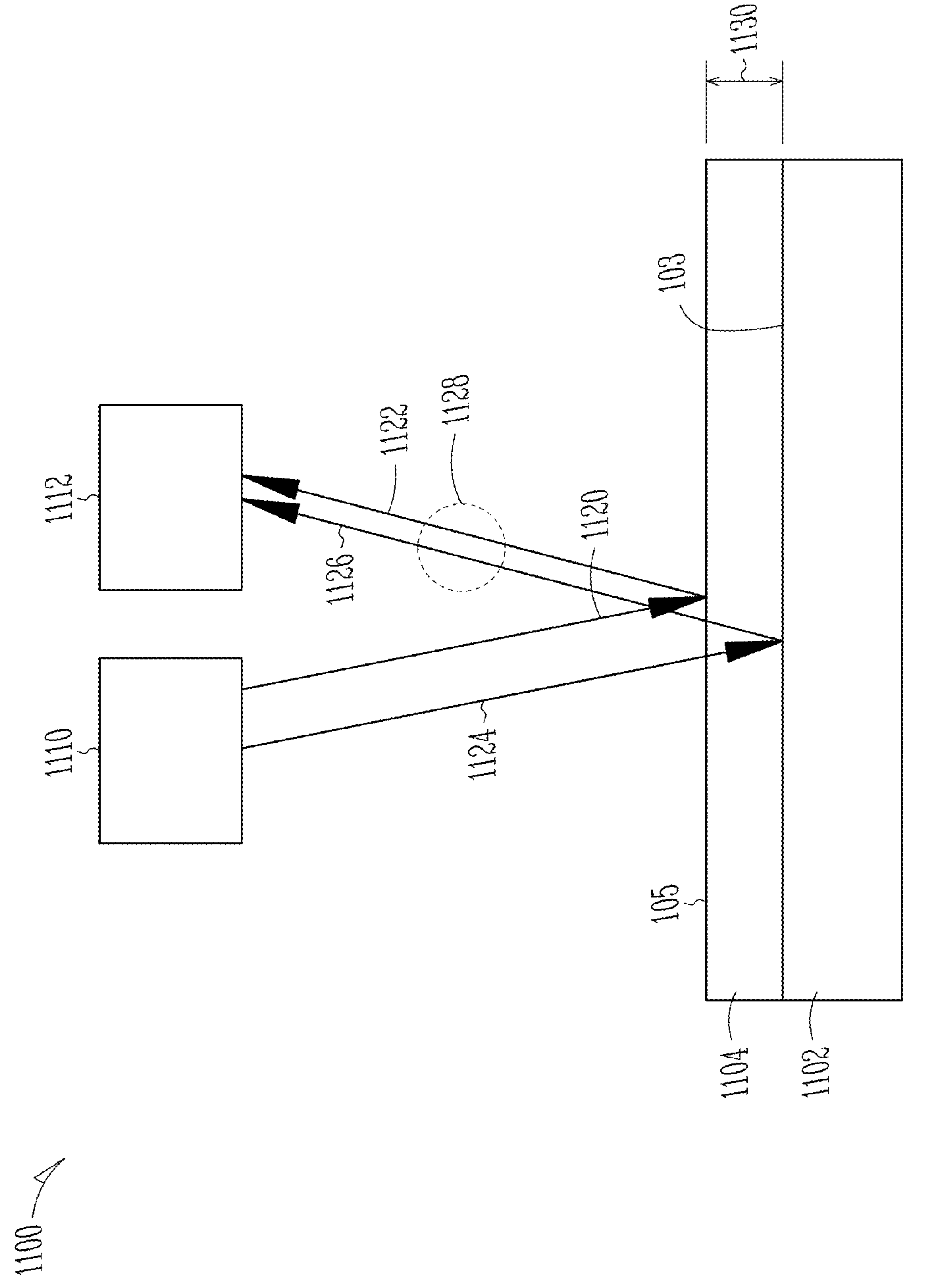
FIG. 11 shows elements of a device and method of inspecting a coating in accordance with some example embodiments.

FIG. 11 illustrates another method of inspecting or otherwise characterizing a coating as described in examples above on a medical device. A portion of a medical device 1102 is shown with a coating 1104. An interface is formed between the coating 1104 and a surface 1103 of the medical device. In one example, the coating is at least partially transparent to allow at least some fraction of light to pass through the coating to the surface 1103 of the medical device and reflect back out again.

FIG. 11 further shows a light source 1110 and a reflected light detector 1112. The term light source may refer to any of a number of energy beams that propagate in a wave. Light emitted from the light source may be in the visible light range, however the invention is not so limited. In one example, the light source 1110 emits ultraviolet light. In one example the light source 1110 emits polychromatic light, such as white light, which is composed of a number of different colors (wavelengths). Although white light is used as an example, other combinations of wavelengths in polychromatic light are also within the scope of the invention. In one example the light source 1110 emits monochromatic light. An example of monochromatic light may include blue light (around 500 nm wavelength) or any other single wavelength of light.

For illustration purposes, the light source 1110 emits a first source beam 1120 that reflects off a surface 1105 of the coating 1104 in a first reflected light beam 1122. The light source 1110 also emits a second source beam 1125 that reflects off the surface 1103 of the medical device 1102 in a second reflected light beam 1126. Due to the thickness 1130 of the coating 1104, there is a travel distance that is different between the first reflected light beam 1122 and the second reflected light beam 1126. The difference will cause wavelength interaction along the return path region 1128 between the first reflected light and the second reflected light. In one example, the wavelength interaction is constructive interference. In one example, the wavelength interaction is destructive interference. The type and magnitude of interaction will depend on factors of the coating, including, but not limited to, thickness, transmittance, index of refraction, etc.

In one example, the wavelength interaction includes a color shift that is detectable by the reflected light detector 1112. In one example the wavelength interaction may also be detectable by the naked eye, although the invention is not so limited. For example, with a polychromatic light source, such as white light, if a blue wavelength of light experiences constructive interference, the color may shift to a bluer color. Conversely, with a polychromatic light source, such as white light, if a blue wavelength of light experiences destructive interference, the color may shift to a less blue color. Although blue is used as an example, the invention is not so limited. A color or wavelength chosen for an indicator will depend on factors discussed above, such as thickness, transmittance, index of refraction, etc. of the coating being inspected.

In one example, the wavelength interaction includes an attenuation or decrease in intensity that is detectable by the reflected light detector 1112. In one example the wavelength interaction may also be detectable by the naked eye, although the invention is not so limited. For example, with a monochromatic light source tailored to an expected thickness of coating, destructive interference can be used to detect the coating by observing or measuring a decrease in intensity. Constructive interference can also be used to detect the coating by observing or measuring an increase in intensity.

In one example, measuring a light change resulting from wavelength interaction indicates a presence or absence of a coating. Very thin transparent coatings can be difficult to detect. Inspection methods as described may be used to indicate whether a coating was deposited at all, and if any regions were missed. In one example, an absence of a light change indicates an absence of a coating. Detection of an absence of a coating may be useful to determine if a coating procedure was performed at all, or if an applied coating is spotty, or only partially applied. One advantage of methods and devices for inspection as described includes the non-contact nature of the inspection. Risk of damaging the coating is minimal due to the lack of contact.

In one example, measuring a light change resulting from wavelength interaction further includes quantifying a thickness of the coating where the quantification is derived from the light change. In one example, deposited coatings are self-limiting, and a coating thickness is generally uniform across a surface. In another example, measuring a light change resulting from wavelength interaction further includes quantifying variations in thickness of the coating derived from the light change. In non-self-limiting examples, it may be useful to measure how consistent a coating thickness is, in order to adjust a process parameter to make a coating more uniform if desired.

In one example, the light detector 1112 includes a spectrometer. In color detection examples as described above, it may be useful to measure small variations in color in a quantifiable and repeatable way. In one example, the spectrometer is an areal spectrometer, that facilitates a surface map indicating thickness variations as described above.

Figure 8:
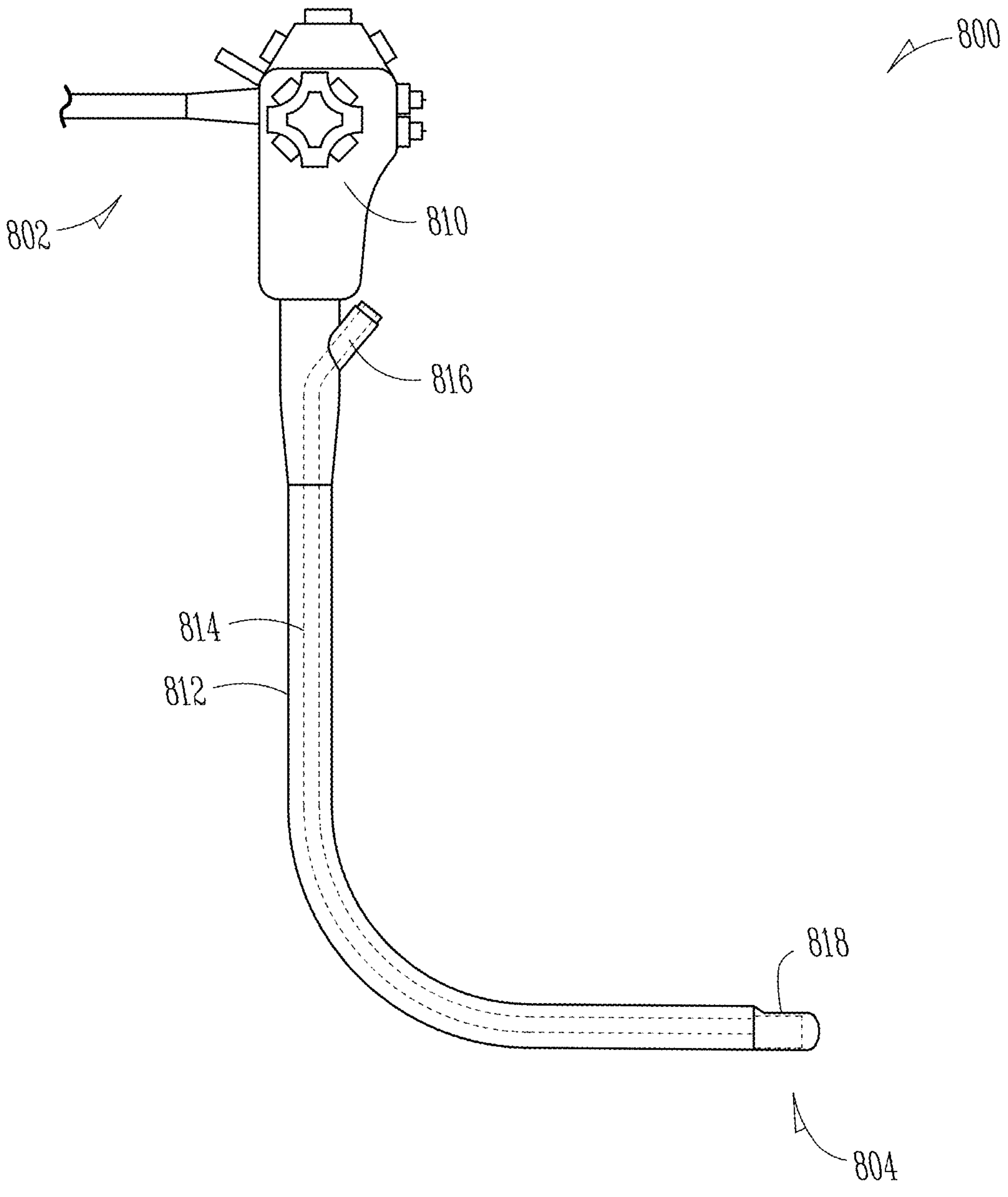
FIG. 8 shows a duodenoscope in accordance with some example embodiments.

FIG. 8 shows another example medical device that includes one or more surfaces with regular periodic physical structure that exhibit low adhesion. The example of FIG. 8 shows a duodenoscope 800. The duodenoscope 800 in the present embodiment includes a main body 802 and a distal end unit 804. An outer lumen 812 is shown between the main body 802 and the distal end unit 840. The outer lumen 812 includes an inner passage 814 for introduction of additional lumens, or other secondary medical devices. Port 816 is shown leading to the inner passage 814, and exiting at opening 818 of the distal end unit 804. Operating controls 810 are optionally located on the main body 802.

Figure 9A:
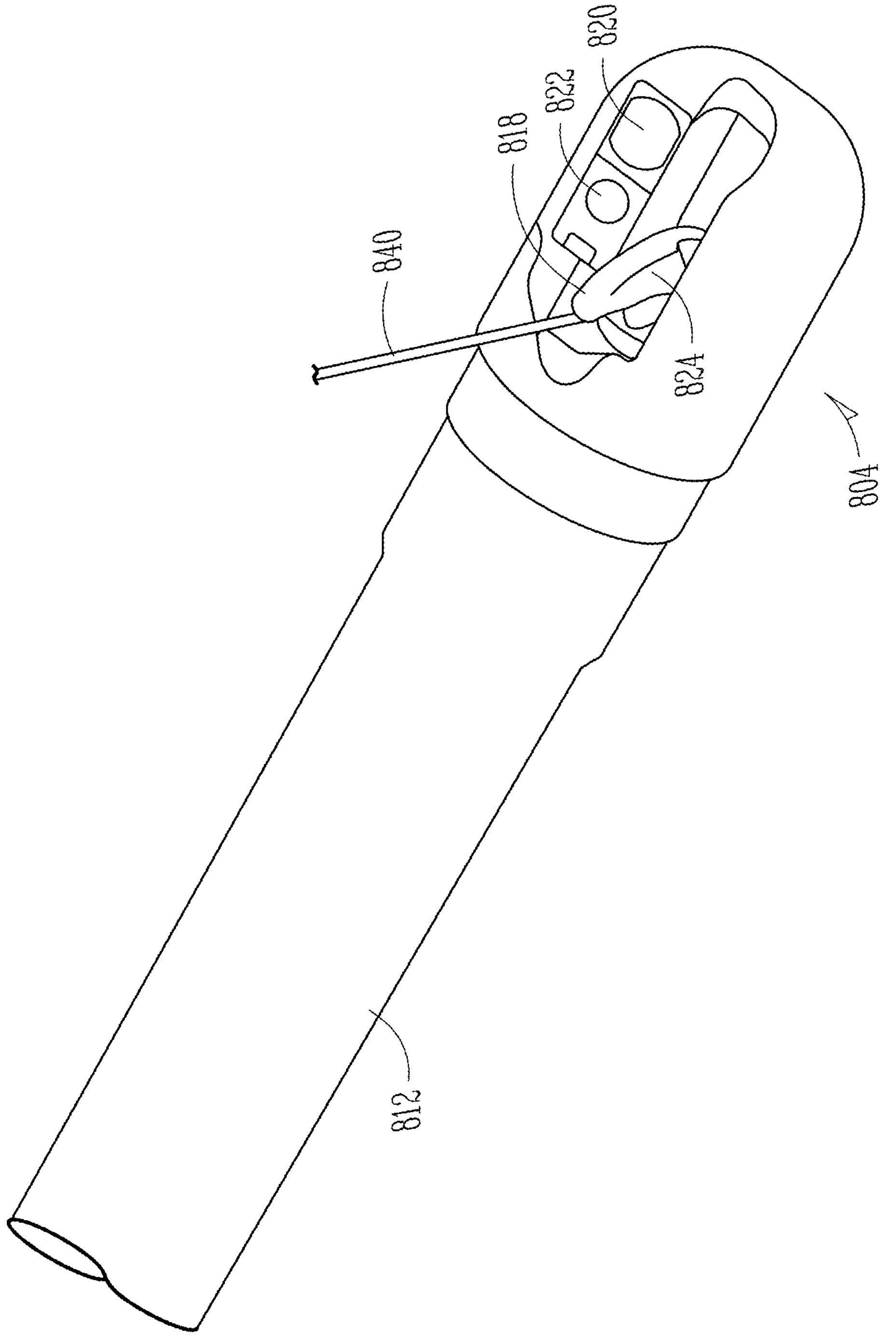
FIG. 9A shows a distal end unit of a duodenoscope in accordance with some example embodiments.

FIG. 9A shows a closer view of distal end unit 804. A portion of the outer lumen 812 is shown coupled to the distal end unit 804. An illumination source 820 and an imaging device 822 are shown. An elevator 824 is illustrated directing a secondary device 840 outward at an angle from the outer lumen 812 through the opening 818. Examples of a secondary device include, but are not limited to, a guide wire, a lumen, an optical fiber device, etc.

Figure 9B:
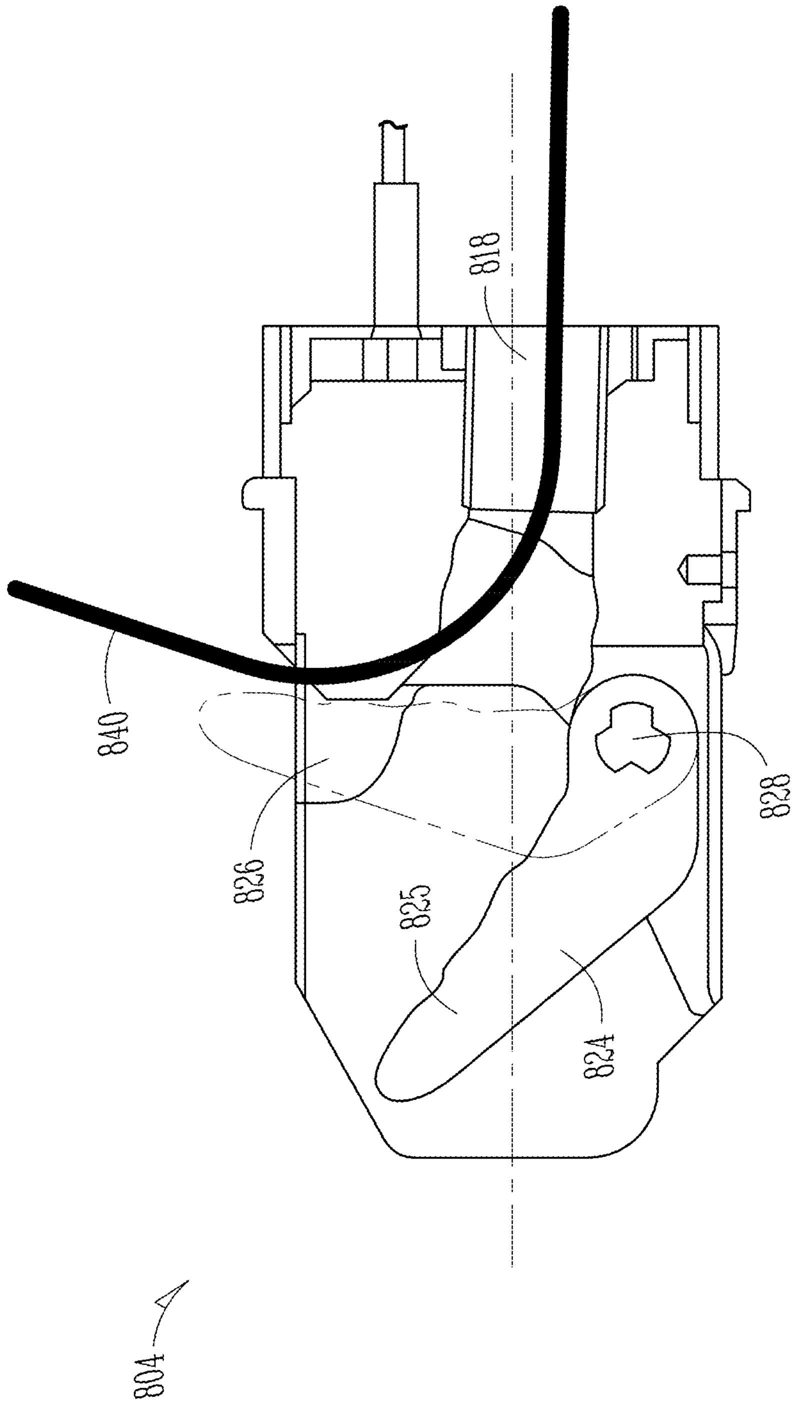
FIG. 9B shows a cross section of a distal end unit of a duodenoscope in accordance with some example embodiments.

FIG. 9B shows the elevator 824 being movable about a pivot 828 between a first position 825, and a second position 826 (shown in dashed ghost lines). FIG. 9B shows the secondary device 840 being diverted by the elevator 824 from the opening 818 of the inner passage 814 at a selected angle.

In operation, the 812 outer lumen is inserted into a duodenum. The secondary device 840 is inserted into the inner passage 814 through the port 816, and exits the inner passage 814 at the distal end unit 804. By controlling the elevator 824, the secondary device 840 is deployed to a selected location accessed within the duodenum. The secondary device 840 is then utilized to perform a desired procedure at the selected location.

Several surfaces of the duodenoscope 800, will benefit from low adhesion. Example surfaces include, but are not limited to, lenses covering the illumination source 820 and the imaging device 822, and surfaces of the outer lumen 812 and inner passage 814. Other surfaces include, but are not limited to, the elevator 824 and pivot 828. In one example, the secondary device 840 will benefit from sliding across a top surface of the elevator 824 more easily with an addition of a low adhesion surface configuration as described in examples above. Rotation about the pivot 828 will also be accomplished more easily with a low adhesion surface configuration as described in examples above that lowers friction between sliding surfaces. Although a number of specific examples of surfaces benefitting from a low adhesion surface are described, other surfaces of any scope device, and more specifically, a duodenoscope are contemplated to include a such a surface as described in examples above.

Figure 10:
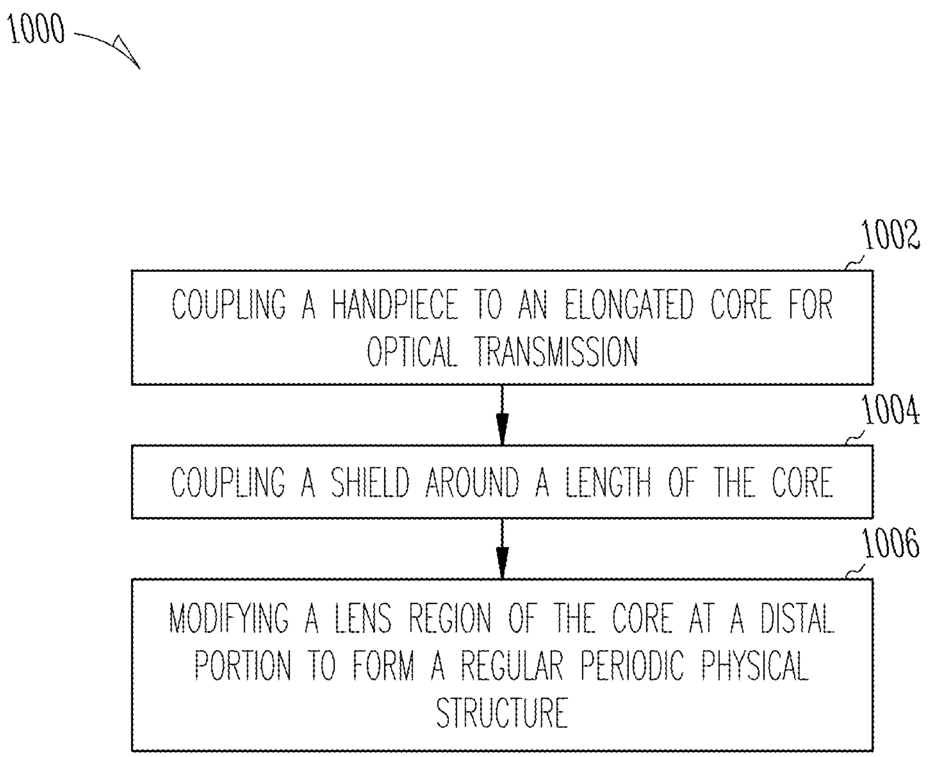
FIG. 10 shows a flow diagram of an example method in accordance with some example embodiments.

FIG. 10 shows a flow diagram of an example method of forming a medical device including a hydrophobic physical structure. In operation 1002, a handpiece is coupled to an elongated core for optical transmission. In operation 1004, a shield is coupled around a length of the core, an in operation 1006, a lens region of the core is modified at a distal portion to form a hydrophobic physical structure.

Several modification/application techniques may be used to form the regular periodic physical structure. As noted above, depending on the specific materials chosen, and the geometry of the regular periodic physical structure, the surface can be formed as hydrophobic, or hydrophilic. One of ordinary skill in the art, having the benefit of the present disclosure, will recognize that a degree of regularity and a degree of periodicity is acceptable, and still falls within the scope of the invention. For example, a deposited nanoparticle coating will have a degree of regularity and periodicity that are determined by a nanoparticle size and how tight a distribution of particle size is. Self-assembly mechanisms of nanoparticles on a surface may also determine a degree of regularity and periodicity. In chemical or laser etched surfaces, a degree of regularity and periodicity may be determined by a photolithography mask, or other method for forming the surface structure.

In one example, a sol-gel process is used. Advantages of sol-gel application include the ability to coat more complex surfaces with high quality films. Challenges of sol-gel may include brittleness, limited thickness options, and induced mechanical stresses in the coating.

In one example, a cold spray process is used. Advantages of cold spray application include the ability to coat at lower temperatures, with low deterioration, low oxidation, and low defects. Challenges of cold spray may include high energy needed for application, high cost, and a limited number of compatible substrates.

In one example, a chemical vapor deposition (CVD) process is used. Advantages of CVD application include a high quality coating, high control of thickness, and the ability to coat complex surfaces. Challenges of CVD may include high temperature requirements, and high cost.

In one example, a physical vapor deposition (PVD) process is used. Advantages of PVD application include the ability to coat inorganic compounds, ecological friendly processes, and a wide variety of available coating materials. Challenges of PVD may include high vacuum chamber requirements and high cost.

In one example, a thermal spray process is used. Advantages of thermal spray application include a large selection of compatible coating materials and substrate materials, and low cost. Challenges of thermal spray may include difficulty in forming thick coatings, low adhesion issues of coatings, and ecologically unfriendly process steps.

In one example, an in-situ polymerization process is used. Advantages of in-situ polymerization include the ability to coat with insoluble polymers. Challenges of in-situ polymerization may include process complexity, high cost, and limited potential for large scale production.

In one example, a spin coating process is used. Advantages of spin coating include high quality coatings, fast drying times, and controllable thicknesses. Challenges of spin coating may include difficulty coating small surfaces and requirements of a smooth surface.

In one example, a dip coating process is used. Advantages of dip coating include the ability to coat complex surfaces and the ability for large scale production. Challenges of dip coating may include undesirable solvent requirements, and limitations of only soluble polymer coatings.

In one example, an electrodeposition process is used. Advantages of electrodeposition include high quality coatings at low cost. Challenges of electrodeposition may include long process times, and conductive substrate requirements.

Although a number of examples of coating processes are provided for forming regular periodic physical structure, the invention is not so limited. Other processes that result in regular periodic physical structure are also within the scope of the invention. It is also noted that coatings formed by the processes described above will result in physical differences, such as microstructures, interface characteristics, etc. that are detectable to one of ordinary skill in the art in a final product upon inspection. As such one of ordinary skill in the art will be able to discern which technique was used to form the regular periodic physical structure by examining the final product.

In one example, application of appropriately sized and spaced nanoparticles using any one or more of the methods described above provides the desired structure of asperities. In one example, a coating may be etched as described above to create all or a part of the desired structure of asperities.

Medical devices having a regular periodic physical structure as described show reduced adhesion over other non-textured coatings for bio materials including, but not limited to, tissues, blood, fats, and/or other biological materials. In particular, lenses having hydrophobic physical structures as described will exhibit both reduced adhesion to bio materials, and will exhibit reduced fogging from moisture present in an operating environment. This provides clearer, less obstructed surfaces such as lenses for a number of possible medical devices, including, but not limited to, endoscopes. In the present disclosure, the term endoscopes includes both rigid and flexible scopes, including telescopes. Medical devices that will benefit from examples disclosed herein may include rigid or flexible scopes, such as endoscopes, medical telescopes and laparoscopes, and the like. Application of regular periodic physical structure to other surfaces of medical devices apart from optical components may further provide advantages such as reduced friction and reduced adhesion where desired.

To better illustrate the method and apparatuses disclosed herein, a non-limiting list of embodiments is provided here:

Example 1 includes an endoscope. The endoscope includes a core for optical transmission, a lens region at a distal portion of the core, and a surface on the lens region, wherein the surface includes a regular periodic physical structure.

Example 2 includes the endoscope of example 1, wherein the regular periodic physical structure includes a Cassie-Baxter state hydrophobic physical structure.

Example 3 includes the endoscope of example 1, wherein the regular periodic physical structure includes a Wenzel state hydrophilic physical structure.

Example 4 includes the endoscope of any one of examples 1-3, wherein the lens region includes multiple lenses.

Example 5 includes the endoscope of any one of examples 1-4, wherein the surface is part of a bulk material that forms the lens region.

Example 6 includes the endoscope of any one of examples 1-5, wherein the surface includes a gaussian hole array.

Example 7 includes the endoscope of any one of examples 1-6, wherein the surface is on a coating that covers at least a portion of the lens region.

Example 8 includes the endoscope of any one of examples 1-7, wherein the coating includes polysiloxane.

Example 9 includes the endoscope of any one of examples 1-8, wherein the coating includes hexamethyldisiloxane (HMDSO).

Example 10 includes the endoscope of any one of examples 1-9, wherein the coating includes fluorosilane.

Example 11 includes the endoscope of any one of examples 1-10, wherein the coating includes one or more fluorophores within the coating.

Example 12 includes an endoscope. The endoscope includes a core for optical transmission, a lens region at a distal portion of the core, a first surface on the lens region, wherein the first surface includes a first regular periodic physical structure, and a second regular periodic physical structure on a second surface of the endoscope wherein the second regular periodic physical structure is different from the first regular periodic physical structure.

Example 13 includes the endoscope of example 12, wherein the first regular periodic physical structure is formed directly from a bulk material of the lens region, and wherein the second regular periodic physical structure is formed from a surface of a coating.

Example 14 includes the endoscope of any one of examples 12-13, wherein the coating includes polysiloxane.

Example 15 includes the endoscope of any one of examples 12-14, wherein the coating includes hexamethyldisiloxane (HMDSO).

Example 16 includes the endoscope of any one of examples 12-15, wherein the coating includes fluorosilane.

Example 17 includes a method of making an endoscope. The method includes coupling a handpiece to an elongated core for optical transmission, coupling a shield around a length of the core, and modifying a lens region of the core at a distal portion to form a regular periodic physical structure.

Example 18 includes the method of example 17, wherein modifying the lens region includes etching the lens region.

Example 19 includes the method of any one of examples 17-18, wherein etching the lens region includes chemical etching.

Example 20 includes the method of any one of examples 17-19, wherein etching the lens region includes laser etching.

Example 21 includes the method of any one of examples 17-20, wherein modifying the lens region includes depositing a coating.

Example 22 includes the method of any one of examples 17-21, wherein depositing a coating includes chemical vapor deposition (CVD).

Example 23 includes the method of any one of examples 17-22, wherein depositing a coating includes physical vapor deposition (PVD).

Example 24 includes the method of any one of examples 17-23, wherein modifying the lens region further including modifying a surface of the coating after deposition.

Example 25 includes the method of any one of examples 17-24, further including illuminating the coating, detecting a first reflected light from the surface of the coating and a second reflected light from an interface between the coating and the surface of the medical device, and measuring a light change resulting from wavelength interaction between the first reflected light and the second reflected light.

Example 26 includes the method of any one of examples 17-25, further including illuminating the coating with a wavelength of electromagnetic radiation, and eliciting a fluorescent emission from a fluorophore within the coating to indicate a presence of the coating.

Example 27 includes an endoscope. The endoscope includes a core for optical transmission, a lens region at a distal portion of the core, and a surface on one or more components at a distal end of the endoscope, wherein the surface includes a regular periodic physical structure.

Example 28 includes the endoscope of example 27, wherein the regular periodic physical structure includes a hydrophobic physical structure.

Example 29 includes the endoscope of any one of examples 27-28, wherein the regular periodic physical structure includes a hydrophilic physical structure.

Example 30 includes the endoscope of any one of examples 27-29, wherein the surface on one or more components at the distal end of the endoscope includes a surface on the lens region.

Example 31 includes the endoscope of any one of examples 27-30, further including a shield covering lateral sides of the core, and wherein the surface on one or more components at the distal end of the endoscope includes a surface on the shield.

Example 32 includes a duodenoscope. The duodenoscope includes a core for optical transmission, the core having a distal end and a proximal end, a lens region at the distal end of the core, and a surface on one or more components adjacent to the distal end of the core, wherein the surface includes a regular periodic physical structure.

Example 33 includes the duodenoscope of example 32, wherein the regular periodic physical structure includes a hydrophobic physical structure.

Example 34 includes the duodenoscope of any one of examples 32-33, wherein the regular periodic physical structure includes a hydrophilic physical structure.

Example 35 includes the duodenoscope of any one of examples 32-34, wherein the surface on one or more components includes an elevator surface.

Example 36 includes the duodenoscope of any one of examples 32-35, wherein the surface on one or more components includes an elevator pivot.

Example 37 includes the duodenoscope of any one of examples 32-36, wherein the surface on one or more components includes a surface on the lens region.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The foregoing description, for the purpose of explanation, has been described with reference to specific example embodiments. However, the illustrative discussions above are not intended to be exhaustive or to limit the possible example embodiments to the precise forms disclosed. Many modifications and variations are possible in view of the above teachings. The example embodiments were chosen and described in order to best explain the principles involved and their practical applications, to thereby enable others skilled in the art to best utilize the various example embodiments with various modifications as are suited to the particular use contemplated.

It will also be understood that, although the terms "first," "second," and so forth may be used herein to describe various elements, these elements should not be limited by these terms. These terms are only used to distinguish one element from another. For example, a first contact could be termed a second contact, and, similarly, a second contact could be termed a first contact, without departing from the scope of the present example embodiments. The first contact and the second contact are both contacts, but they are not the same contact.

The terminology used in the description of the example embodiments herein is for the purpose of describing particular example embodiments only and is not intended to be limiting. As used in the description of the example embodiments and the appended examples, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The invention claimed is:

1. An endoscope comprising:

a core for optical transmission;

a lens region at a distal portion of the core;

a surface on the lens region, wherein the surface includes a regular periodic physical structure;

wherein the surface is on a first coating that covers at least a portion of the lens region, and wherein the first coating includes a first fluorophore configured to provide a first luminescent emission in a presence of electromagnetic radiation; and a second coating including a second fluorophore different from the first fluorophore configured to provide a second luminescent emission different from the first luminescent emission in a presence of second electromagnetic radiation.

2. The endoscope of claim 1, wherein the regular periodic physical structure includes a Cassie-Baxter state hydrophobic physical structure.

3. The endoscope of claim 1, wherein the regular periodic physical structure includes a Wenzel state hydrophilic physical structure.

4. The endoscope of claim 1, wherein the lens region includes multiple lenses.

5. The endoscope of claim 1, wherein the surface includes a gaussian hole array.

6. The endoscope of claim 1, wherein the first coating includes polysiloxane.

7. The endoscope of claim 1, wherein the first coating includes hexamethyldisiloxane (HMDSO).

8. The endoscope of claim 1, wherein the first coating includes fluorosilane.

9. The endoscope of claim 1, further including a second regular periodic physical structure on a second surface of the endoscope wherein the second regular periodic physical structure is different from the regular periodic physical structure of the surface on the lens region.

10. The endoscope of claim 1, wherein the endoscope includes a duodenoscope, and wherein a surface on one or more components adjacent to a distal end of the core includes a second regular periodic physical structure.

11. The endoscope of claim 10, wherein the surface on one or more components includes an elevator surface.

12. The endoscope of claim 10, wherein the surface on one or more components includes an elevator pivot.

13. The endoscope of claim 1, wherein an amount of fluorophores including the first fluorophore and the second fluorophore are included in the coating in an amount less than 10 wt %.

* * * * *